United States Patent [19]

Bolis et al.

[11] 4,329,285
[45] May 11, 1982

[54] FORMYL DERIVATIVES OF HYDRAZINOPENICILLINS

[75] Inventors: Goffredo Bolis, Bergamo; Roberto Giani, Milan; Mario Pinza, Corsico; Giorgio Pifferi; Giampietro Broccali, both of Milan, all of Italy

[73] Assignee: C R A F Sud, Rome, Italy

[21] Appl. No.: 221,365

[22] Filed: Dec. 29, 1980

[30] Foreign Application Priority Data

Dec. 27, 1979 [IT] Italy .................. 28399 A/79

[51] Int. Cl.$^3$ .................. C07D 499/68; C07D 499/70
[52] U.S. Cl. .................. 260/239.1; 424/271
[58] Field of Search .................. 260/239.1; 424/271

[56] References Cited

U.S. PATENT DOCUMENTS 3,174,964  3/1965  Hobbs et al. .................. 260/239.1
4,008,220  2/1977  Tobiki et al. .................. 260/239.1
4,231,927  11/1980  Monguzzi et al. .................. 160/239.1

FOREIGN PATENT DOCUMENTS 1048907  11/1966  United Kingdom .
1509200  5/1978  United Kingdom .
1524950  9/1978  United Kingdom .

*Primary Examiner*—Natalie Trousof
*Assistant Examiner*—Vera C. Clarke
*Attorney, Agent, or Firm*—Stevens, Davis, Miller & Mosher

[57] ABSTRACT

Formyl derivatives of hydrazinopenicillins of the formula

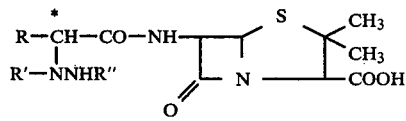

wherein R is thienyl or phenyl, R' is hydrogen, formyl or alkyl containing from 1 to 3 carbon atoms and R" is hydrogen or formyl, provided that at least one of R' and R" is a formyl group, the carbon atom with the asterisk indicating a center of asymmetry of the molecule, and pharmaceutically acceptable salts and esters thereof, as mixture or as separated epimers. These compounds have antibacterial activity against Gram-negative and Gram-positive bacteria and are prepared by a process wherein the corresponding hydrazinopenicillin is reacted under anhydrous conditions with acetoformic anhydride to give the desired compounds.

8 Claims, No Drawings

FORMYL DERIVATIVES OF HYDRAZINOPENICILLINS

The present invention is concerned with new penicillins and more particularly with formyl derivatives of hydrazinopenicillins.

In our previous patent application No. 31,558 A of Nov. 10, 1972 new hydrazino derivatives of penicillins of the general formula

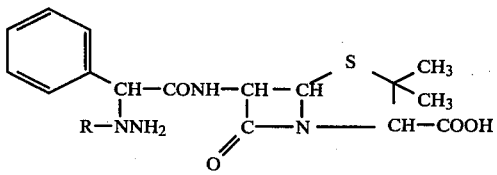

Ia wherein R is hydrogen or alkyl containing up to 6 carbon atoms, as well as its non-toxic salts, either as a mixture or as separated epimers, were described.

We have now found and this is one of the objects of the present invention, that by replacing the hydrogen atoms of the nitrogen in position 1 and/or 2 of the hydrazino group in compounds of formula Ia and in its carboxylic derivatives, new penicillins displaying interesting antibacterial activity are obtained.

Formyl derivatives of hydrazinopenicillins I, in which the phenyl group is substituted with a heterocyclic group, are a further object of the present invention.

Compounds belonging to the class having the general formula

I

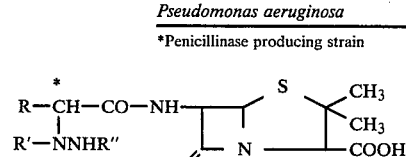

wherein R is phenyl or thienyl, R' is hydrogen, alkyl containing 1 to 3 carbon atoms as, formyl and R" is hydrogen or formyl provided that at least one of R' and R" be a formyl group, the carbon atom having the asterisk indicating a center of asymmetry of the molecule, in the form of mixture or separated epimers, are prepared and hereinafter described.

The invention further includes suitable pharmaceutically acceptable esters and salts of penicillane derivatives of formula I.

The new formylhydrazino penicillins of formula I are prepared starting from hydrazino penicillins of the formula

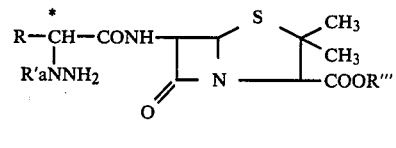

II wherein R is phenyl or thienyl, R'a is hydrogen or alkyl having from 1 to 3 carbon atoms and R''' is hydrogen or a pharmaceutically acceptable, such as pivaloyloxymethyl and 1-(ethoxycarbonyloxy) ethyl, the carbon atom having the asterisk indicating a center of asymmetry of the molecule, in the form of a mixture or separated epimers, by reaction under anhydrous conditions with mixed acetoformic anhydride. The formylating reaction is carried out in an organic solvent suitable for the reagent materials, such as for example a tertiary organic base or an aprotic, optionally halogenated solvent.

Compounds of the present invention can also be prepared by standard procedures known in the art such as for example by reacting 6β-amino-penicillanic acid optionally esterified with a suitable derivative, already formylated, at the substituted α-hydrazino acetic acid.

The compounds of the present invention display interesting anti-bacterial activity against Gram-positive and Gram-negative bacteria. The minimum inhibiting concentration (MIC) in vitro of the compounds of the invention expressed in γ/ml are listed in the following Table.

The following Examples are given for the purpose of illustrating the present invention without limiting it.

| Microorganisms | (R) 6β-[α-(2-formyl-1-methyl hydrazino)phenylacetamido] penicillanic acid | (R) 6β-[α-(1.2-diformyl-hydrazino)phenylacetamido]penicillanic acid | (R) 6β-[α-(2-formylhydrazino)phenylacetamido]penicillanic acid |
|---|---|---|---|
| Staphylococcus aureus | 0.19 | 0.19 | 0.048 |
| Staphylococcus aureus* | 3.12 | 6.25 | 1.56 |
| Streptococcus pyogenes | 0.048 | 0.097 | <0.012 |
| Streptococcus pneumoniae | 0.024 | 0.024 | 0.012 |
| Streptococcus foecalis | 3.12 | 6.25 | 1.56 |
| Sarcina lutea | 0.012 | 0.024 | <0.012 |
| Escherichia coli | 1.56 | 3.12 | 0.78 |
| Shigella dysenteriae | 1.56 | 3.12 | 0.78 |
| Salmonella typhi | 3.12 | 6.25 | 1.56 |
| Salmonella typhymurium | 12.5 | 25 | 3.12 |
| Salmonella enteritidis | 25 | 25 | 6.25 |
| Neisseria meningitidis | 0.012 | 0.097 | <0.012 |
| Pseudomonas aeruginosa | >200 | >200 | 200 |

*Penicillinase producing strain

EXAMPLE 1

Pivaloyloxymethyl ester of (R) 6β-[α-(2-formylhydrazino)phenylacetamido]penicillanic acid A solution consisting of 3 g R(−)α-[1-(p.nitrobenzyloxycarbonyl)hydrazino]phenylacetic acid in 20 ml formic acid stirred at 4° C. is treated dropwise with 10 ml acetoformic anhydride under stirring for 10 minutes and then for a further hour at ambient temperature. The product is evaporated to dryness and the residue is taken up several times with diethyl ether until there is obtained a solid compound which is triturated with diethyl ether, taken up under vacuum to give 3.06 g R(−)α-[1-(p.nitrobenzyloxycarbonyl)-2-formylhydrazino]phenylacetic acid melting at 158°–161° C. (with decomposition); $[\alpha]_D = -82.47°$ C. (c = 1 in tetrahydrofuran).

0.78 grams of dicyclohexylcarbodiimide are added to a solution of 1.20 g pivaloyloxymethyl ester of 6β-aminopenicillanic acid in 5 ml tetrahydrofuran, while stirring at 4° C., and then dropwise, 1.4 g R(−)α-[1-(p.nitrobenzyloxycarbonyl)-2-formylhydrazino]-phenylacetic acid diluted in 8 ml tetrahydrofuran are added. Stirring is continued at 4° C. for a further 10 minutes and then at ambient temperature for 30 minutes. The insoluble residue is filtered off, evaporated to dryness, taken up with 30 ml methylene chloride, washed twice with 10 ml solution of 5% sodium bicarbonate and 10 ml water; it is then made anhydrous and evaporated to dryness. The residue is triturated with diisopropyl ether and purified by chromatography (silicagel, diethyl ether 100%): 1.93 g pivaloyloxymethyl ester of (R) 6β-{α-[1-(p.nitrobenzyloxycarbonyl-2-formylhydrazino)phenylacetamido]}penicillanic acid are obtained melting at 76°–78.5° C. (with decomposition); $[\alpha]_D = +55.5°$ (c = 1 in tetrahydrofuran).

To a solution consisting of 1.2 g pivaloyloxymethyl ester of (R) 6β-{α-[1-(p.nitrobenzyloxycarbonyl-2-formylhydrazino)phenylacetamido]}penicillanic acid in 10 ml of 95% ethyl alcohol and 3 ml water are added, under stirring, 1.8 g of 5% Palladium/charcoal. Hydrogen is bubbled in for 20 hours. It is filtered over celite, evaporated to dryness and taken up several times with ether until a solid is obtained. The product is then triturated with diisopropyl ether and taken up under vacuum. It is purified by chromatography (silicagel, hexane/ethyl acetate 1:1) to obtain 0.20 g pivaloyloxymethyl ester of R 6β-[α-(2-formylhydrazino)-phenylacetamido]penicillanic acid melting at 69.3°–74.8° C. (with decomposition).

EXAMPLE 2

(R,S) 6β-[α-(1-formylhydrazino)phenylacetamido]penicillanic acid

A solution consisting of 1.86 ml formic acid in 7.5 ml diethyl ether, cooled to −15° C. is treated with a solution of 3.43 g dicyclohexylcarbodiimide in 10 ml diethyl ether and stirred for 30 minutes. To the so obtained mixture is added a suspension in methylene chloride of (R,S) α-(2-benzyloxycarbonylhydrazino)phenylacetic acid trimethylsilylester obtained by refluxing the free acid with hexamethyldisilazane in acetonitrile and stirring at 0° C. for 2 hours. Fifty milliliters of cold water are added thereto and the pH adjusted to 9. The solid residue is filtered off and the layers are separated. The aqueous layer, acidified to pH 1.5, is extracted three times with 50 ml methylene chloride, the organic extracts collected together and washed with 20 ml water, made anhydrous and evaporated to dryness to give 2.64 g (R,S) α-(1-formyl-2-benzyloxycarbonylhydrazino)-phenylacetic acid in the oily form from which the corresponding sodium salt is obtained melting at 148°–150° C. (with decomposition). To a solution of 10 g of the sodium salt of (R,S) α-(1-formyl-2-benzyloxycarbonyl-hydrazino)phenylacetic acid in 85 ml acetone cooled to −40° C., are added 2.95 ml ethyl chloroformiate and then the mixture is stirred for 30 minutes. An aqueous-acetonic solution (30 ml) containing 5.85 g of the triethylamine salt of 6β-aminopenicillanic acid is added thereto and the mixture is stirred at −25° C. for 45 minutes. Then 50 ml cold water and 150 ml methylene chloride are added to the mixture and this is acidified to pH 2. The layers are then separated and the organic one is washed with 50 ml water, made anhydrous and evaporated to dryness. The residue is triturated with cyclohexane and there are obtained 13 g (R,S) 6β-[α-(1-formyl-2-benzyloxycarbonylhydrazino)phenylacetamido]-penicillanic acid melting at 98°–100° C. (with decomposition).

To a solution of 1.16 g sodium bicarbonate in 37.5 ml water are added 7.3 g (R,S) 6β-[α-(1-formyl-2-benzyloxycarbonylhydrazino)phenylacetamido]penicillanic acid and 5.25 g 10% palladium over charcoal. Hydrogen is bubbled in for 2 hours, then the catalyst is filtered off and the filtrate is stratified with 130 ml methylene chloride, cooled to 0° C. and acidified to pH 2. The layers are separated, the organic one is extracted twice with 20 ml methylene chloride and the organic extracts collected together are washed three times with 30 ml water, made anhydrous and evaporated to dryness. 2.15 grams (R,S) 6β-[α-(1-formylhydrazino)-phenylacetamido]penicillanic acid are obtained, melting at 156°–160° C. (with decomposition).

EXAMPLE 3

(R) 6β-[α-(2-Formylhydrazino)phenylacetamido]penicillanic acid

To a solution of 2.26 g p.nitrobenzyl ester of 6β-aminopenicillanic acid in 10 ml tetrahydrofuran stirred at 4° C. are added 1.33 g dicyclohexylcarbodiimide. Then 2.40 g R(−)α-[1-(p.nitrobenzyloxycarbonyl-2-formylhydrazino)]phenylacetic acid dissolved in 20 ml tetrahydrofuran (obtained in a manner similar to that described in Example 1) are added thereto. The mixture is further stirred at 4° C. for 10 minutes, and at ambient temperature for 3 hours, then the residue is removed by filtration and the filtrate evaporated to dryness, and taken up several times with diethyl ether until a solid is obtained. It is dissolved in 50 ml ethyl acetate, washed three times with 10 ml of 5% sodium bicarbonate solution, made anhydrous and evaporated to dryness. It is purified by chromatography (silicagel, hexane/ethyl acetate 3:7) to give 3.42 g p.nitrobenzyl ester of (R)6β-{α-[1-(p.nitrobenzyloxycarbonyl)-2-formylhydrazino]}phenylacetamido penicillanic acid (4b) melting at 101.5°–104.7° C. (with decomposition); $[\alpha]_D = +74.47°$ C. (c = 1 in tetrahydrofuran).

To a solution of 2.20 g p.nitrobenzyl ester of (R) 6β-{α-[1-(p.nitrobenzyloxycarbonyl)-2-formylhydrazino]}phenylacetamido penicillanic acid in 30 ml tetrahydrofuran and 14 ml water are added, under stirring, 4.50 g 5% palladium/calcium carbonate. Hydrogen is bubbled in for 20 hours, it is filtered over celite and evaporated to dryness. The residue is triturated with ether, collected under vacuum and dissolved in 5.5 ml tetrahydrofuran and 1 ml water. Fifty milliliters of isopropyl alcohol are added to the solution stirred at 4° C., stirring is further continued for 10 minutes, then the solid residue is collected under vacuum and 1.09 g (R) 6β-[α-(2-formylhydrazino)phenylacetamido]penicillanic acid as calcium salt are obtained, melting at 200° C. (with decomposition).

EXAMPLE 4

1-(Ethoxycarbonyloxy)ethyl ester of (R) 6β-[α-(2-formylhydrazino)]phenylacetamido penicillanic acid To a solution of 1.21 g 1-(ethoxycarbonyloxy)ethyl ester of 6β-aminopenicillanic acid in 5 ml tetrahydrofuran, cooled to 4° C., 0.78 g dicyclohexylcarbodiimide are added and then treated dropwise with a solution of 1.40 g R(−) α-[1-(p.nitrobenzyloxycarbonyl)-2-formylhydrazino]phenylacetic acid (prepared in a manner similar to that described in Example 1). The product is stirred at ambient temperature for 30 minutes. The solid is filtered off and the filtrate is evaporated to dryness. The residue is dissolved in 30 ml methylene chloride, washed twice with 5% sodium bicarbonate solution and with 10 ml water, then made anhydrous and evaporated to dryness. The residue is purified by chromatography (silicagel, ether) and 1.6 g 1-(ethoxycarbonyloxy)ethyl ester of (R) 6β-α-[1-(p.nitrobenzyloxycarbonyl)-2-formylhydrazino]phenylacetamido penicillanic acid are obtained, melting at 89.3°–97.3° C.

To a solution of 1.20 g 1-(ethoxycarbonyloxy)ethyl ester of (R) 6β-α-[1-(p.nitrobenzyloxycarbonyl)-2-formylhydrazino]phenylacetamido penicillanic acid in 10 ml 95% ethyl alcohol and 3 ml water are added 1.80 g 5% palladium over calcium carbonate, and hydrogen is bubbled in for 20 hours. The catalyst is filtered off, the mixture evaporated to dryness, then the residue purified by chromatography (silicagel, hexane/ethyl acetate 1:1) to give 0.43 g 1-(ethoxycarbonyloxy)ethyl ester of (R) 6β-[α-(2-formylhydrazino)phenylacetamido]penicillanic acid, melting at 58.6°–64.3° C.; $[\alpha]_D = +111.3°$ (c=1 in chloroform).

EXAMPLE 5

Pivaloyloxymethyl ester of (R) 6β-[α-(1.2-diformylhydrazino)phenylacetamido]-penicillanic acid Three milliliters of acetoformic anhydride are added dropwise to a solution of 1 g R(−)α-hydrazinophenyl acetic acid in 3 ml formic acid, while stirring at 4° C., and stirring is continued for a further 10 minutes, then for a further 30 minutes at ambient temperature. The product is evaporated to dryness and taken up with diethyl ether and the solid obtained collected under vacuum to give 0.94 g R(−)α-(1.2-diformylhydrazino)-phenylacetic acid melting at 141.7°–155.4° C. (with decomposition); $[\alpha]_D = -222.5°$ C. (c=1 in tetrahydrofuran).

To a solution of 2.97 g pivaloyloxymethyl ester of 6β-amminopenicillanic acid in 10 ml tetrahydrofuran stirred at 4° C., 1.85 g dicyclohexylcarbodiimide are added, and 2 g R(−)α-(1.2-diformylhydrazino)phenylacetic acid dissolved in 30 ml tetrahydrofuran are added dropwise thereto. Stirring is continued for 10 minutes at 4° C. and then for a further 2 hours at ambient temperature. The product is then filtered, the filtrate dried and the residue triturated with diisopropylether, collected under vacuum and chromatographed (silicagel, hexane/ethyl acetate 3:7) to give 2.4 g pivaloyloxymethyl ester of (R) 6β-[α-(1.2-diformylhydrazino)-phenylacetamido]penicillanic acid melting at 91.7°–93.1° C.; $[\alpha]_D = +96.42°$ C. (c=1 in tetrahydrofuran).

EXAMPLE 6

Pivaloyloxymethyl ester of 1 g (R,S) 6β-[α-(1.2-diformylhydrazino)-2-thienylacetamido]-penicillanic acid A solution of 1 g (RS) α-hydrazino-2-thienylacetic acid in 3 ml formic acid is stirred at 4° C. and treated dropwise with a solution of 3 ml acetoformic anhydride. Stirring is continued for 20 minutes at the same temperature and for a further 30 minutes at ambient temperature, then the product is evaporated to dryness, taken up with diethyl ether and the so obtained solid is triturated with ethyl ether collected under vacuum, to give 1.26 g (RS) α-(1.2-diformylhydrazino)-2-thienylacetic acid melting at 168°–170° C. (with decomposition).

To a solution of 1.1 g pivaloyloxymethyl ester of 6β-aminopenicillanic acid in 3 ml tetrahydrofuran stirred at ambient temperature are added 686 mg dicyclohexylcarbodiimide and dropwise 760 mg (RS) α-(1.2-diformylhydrazino)-2-thienylacetic acid dissolved in 20 ml tetrahydrofuran. The mixture is stirred for one hour and a half, the residue is removed, the filtrate evaporated to dryness and the residue triturated with diisopropylether, collected under vacuum and purified by chromatography (silicagel, hexane/ethyl acetate 3:7) to obtain 1.25 g (69%) pivaloyloxymethyl ester of (RS) 6β-[α-(1.2-diformylhydrazino)-2-thienylacetamido]-penicillanic acid melting at 67.4° C.; $[\alpha]_D = +147.2°$ C. (c=1 in tetrahydrofuran).

EXAMPLE 7

Pivaloyloxymethyl of (R) 6β-[α-(1-methyl-2-formylhydrazino)phenylacetamido]-penicillanic acid To a solution of 5 g (R) α-(1-methylhydrazino)-phenylacetic acid in 10 ml formic acid, kept under stirring at 4° C., 15 ml acetoformic anhydride are added dropwise, and the mixture is stirred at 4° C. for 15 minutes and then an hour and a half at ambient temperature. The product is evaporated to dryness and the oily residue taken up with 30 ml methylene chloride and 30 ml water, then adjusted to pH 7.2, the aqueous layer is washed with methylene chloride, stratified with 50 ml methylene chloride, adjusted to pH 2 and extracted with methylene chloride. The organic layers are collected, made anhydrous, evaporated to dryness and triturated with diethyl ether to give a solid residue, which is collected under vacuum, consisting of 3.46 g (R) α-(2-formyl-1-methylhydrazino) phenylacetic acid melting at 129°–131° C.; $[\alpha]_D = 104.8°$ C. (c=1 in 0.1 N sodium hydroxide).

To a solution of 0.50 g (R) α-(2-formyl-1-methylhydrazino)phenylacetic acid and 0.34 ml triethylamine in 5 ml tetrahydrofuran at −50° C., 0.25 ml ethyl chloroformiate are added, the mixture is stirred at −20° C. for 30 minutes, then a solution of 0.72 g pivaloyloxymethyl ester of 6β-aminopenicillanic acid in 8 ml tetrahydrofuran are added thereto. The mixture is stirred at 0° C. for 1 hour, thereafter 20 ml methylene chloride and 20 ml water are added. The layers are separated and the organic one is washed twice with 10 ml solution of 5% sodium bicarbonate and 10 ml water. The product is made anhydrous and evaporated to dryness, the residue is purified through chromatography (silicagel, hexane/ethyl acetate 10:2) to give 0.30 g pivaloyloxymethyl ester of (R) 6β-[α-(1-methyl-2-formylhydrazino)phenylacetamido]penicillanic acid melting at 147°–154.3° C. (with decomposition); $[\alpha]_D = +129.4°$ C. (c=0.5 in chloroform).

EXAMPLE 8

1-(Ethoxycarbonyloxy)ethyl ester of (R) 6β-[α-(1-methyl-2-formylhydrazino)phenylacetamido]penicillanic acid In a manner analogous to that described above, using 1-(ethoxycarbonyloxy)ethyl ester of 6β-aminopenicillanic acid, 1-(ethoxycarbonyloxy)ethyl ester of (R) 6β-[α-(1-methyl-2-formylhydrazino)phenylacetamido]penicillanic acid is obtained, melting at 71.3°–77.4° C. (with decomposition); $[\alpha]_D = 131.6°$ C. (c=0.5 in chloroform).

EXAMPLE 9

(R) 6β-[α-(1.2-Diformylhydrazino)phenylacetamido]penicillanic acid

A solution of 0.5 g R 6β-(α-hydrazinophenylacetamido)penicillanic acid in 6 ml pyridine, stirred at 4° C., is treated dropwise with 1.5 ml acetoformic anhydride solution and kept under stirring for a further 5 hours. Then it is washed three times with 10 ml hexane and the oily residue is triturated with 30 ml diethyl ether and collected under vacuum to give 0.38 g (R) 6β-[α-(1.2-diformylhydrazino)phenylacetamido]penicillanic acid melting at 137°–177° C. (with decomposition).

The corresponding sodium salt, obtained by treatment with a solution of 2-ethylhexanoate sodium in isopropyl alcohol, melts at 180° C. (with decomposition).

EXAMPLE 10

(R) 6β-[α-(2-Formyl-1-methylhydrazino)-phenylacetamido]penicillanic acid

A solution of 2 g (R) 6β-[α-(1-methylhydrazino)-phenylacetamido]penicillanic acid in 15 ml pyridine, under stirring at 4° C., is treated dropwise with 6 ml acetoformic anhydride and kept under stirring for a further 30 minutes at the same temperature. The mixture is washed with hexane until there is obtained a thick oily product, which is triturated with 50 ml diethyl ether three times, and under vacuum 1.5 g (R) 6β-[α-(2-formyl-1-methylhydrazino)phenylacetamido]penicillanic acid is separated, melting at 157°–158.1° C. (with decomposition); $[\alpha]_D = +201.51°$ C. (c=1 in tetrahydrofuran).

EXAMPLE 11

(R) 6β-[α-(2-Formylhydrazino)phenylacetamido]penicillanic acid

To a solution consisting of 5 g (R) 6β-(α-hydrazinophenylacetamido)penicillanic acid and 5.4 ml triethylamine in 100 ml methylene chloride cooled to −20° C. are added dropwise 2.3 ml acetoformic anhydride solution in 20 ml methylene chloride. The mixture is stirred at −20° C. for 30 minutes, then at ambient temperature for 1 hour. It is evaporated to dryness and the residue is diluted with 80 ml of 3.5% sodium bicarbonate. It is stratified with 40 ml ethyl acetate and the layers are separated: the aqueous layer, adjusted to pH 2 with 10% hydrochloric acid, is again stratified with 100 ml ethyl acetate. The layers are separated and the organic one, made anhydrous, is concentrated, the solid removed by filtration, and the clear filtrate is evaporated to dryness. The residue, triturated with diethyl ether, gives 2.6 (R) 6β-[α-(2-formylhydrazino)phenylacetamido]penicillanic acid melting at 145.5°–147.8° C. (with decomposition); $[\alpha]_D = +133.8°$ C. (c=1 in tetrahydrofuran).

EXAMPLE 12

Pivaloyloxymethyl ester of (R) 6β-[α-(1-methyl-2-formylhydrazino)phenylacetamido]penicillanic acid To a solution of 3.3 g pivaloyloxymethyl ester of 6β-aminopenicillanic acid in 30 ml methylene chloride cooled to 0° C. are added 13 ml propylene oxide, while stirring, and then to −30° C. 2.3 g chloride hydrochloride of (R) α-(1-methylhydrazino)phenylacetic acid are added, and the product is kept under stirring for 30 minutes at −20° C. and for a further 2 hours at 0° C. Then, it is evaporated to dryness, the residue is triturated with diisopropyl ether, and 4.2 g pivaloyloxymethyl ester of (R) 6β-[α-(1-methylhydrazino)phenylacetamido]penicillanic acid hydrochloride are obtained, melting at 88°–90° C. (with decomposition); $[\alpha]_D = +140.53°$ C. (c=1 in methyl alcohol).

A solution of 4 g pivaloyloxymethyl ester of (R) 6β-[α-(1-methylhydrazino)phenylacetamido]penicillanic acid in 25 ml anhydrous pyridine is cooled to 4° C., and 4.2 ml acetoformic anhydride are added dropwise thereto. The product is kept under stirring at 4° C. for 30 minutes, then evaporated to dryness and the residue dissolved in 100 ml ethyl acetate and washed with water. The organic layer is made anhydrous and evaporated to dryness, then the residue purified by chromatography (silicagel, hexane:ethyl acetate, 10:2) gives 2.50 g pivaloyloxymethyl ester of (R) 6β-[α-(1-methyl-2-formylhydrazino)phenylacetamido]penicillanic acid melting at 147°–154.3° C. (with decomposition); $[\alpha]_D = +129.4°$ C. (c=0.5 in chloroform).

EXAMPLE 13

1-(Ethoxycarbonyloxy)ethyl ester of (R) 6β-[α-(1-methyl-1-formylhydrazino)phenylacetamido]penicillanic acid Twenty-four milliliters of propylene oxide are added to a solution of 6 g 1-(ethoxycarbonyloxy)ethyl ester of 6β-aminopenicillanic acid in 60 ml methylene chloride; the mixture is cooled to −30° C. and while stirring 4.25 g chloride hydrochloride of (R) α-(1-methylhydrazino)phenylacetic acid are added thereto. The temperature is maintained at −30° C. for 30 minutes, then increased to ambient temperature and the product is kept under stirring for a further hour. The mixture is evaporated to dryness, the residue is triturated with diethyl ether, treated with sodium bicarbonate and 7 g 1-(ethoxycarbonyloxy)ethyl ester of (R) 6β-[α-(1-methylhydrazino)phenylacetamido]penicillanic acid melting at 45.6°–47° C. (with decomposition); $[\alpha]_D = +76.7°$ C. (c=0.5 in chloroform).

Ten milliliters of acetoformic anhydride are added dropwise to a solution of 5 g 1-(ethoxycarbonyloxy)ethyl ester of (R) 6β-[α-(1-methylhydrazino)phenylacetamido]penicillanic acid in 40 ml anhydrous pyridine, cooled to 4° C. and kept under stirring for 30 minutes. To that mixture 150 ml ethyl acetate are added, it is washed four times with 100 ml water, the organic layer, after separation, is made anhydrous and evaporated to dryness. The residue is purified by chromatography (silicagel, ethyl acetate/hexane, 9:1) to give 2.20 g 1-(ethoxycarbonyloxy)ethyl ester of (R) 6β-[α-(1-methyl-2-formylhydrazino)phenylacetamido]penicillanic acid melting at 71.3°–77.4° C. (with decomposition); $[\alpha]_D = +131.6°$ C. (c=0.5 in chloroform).

EXAMPLE 14

1-(Ethoxycarbonyloxy)ethyl ester of (R) 6β-[α-(1-methyl-2-formylhydrazino)phenylacetamido]penicillanic acid To a solution of 0.80 g (R) 6β-[α-(1-methyl-2-formylhydrazino)phenylacetamido]penicillanic acid in 5 ml dimethylsulphoxide are added 0.28 ml triethylamine and 0.30 g α-chlorodiethylcarbonate. The mixture is stirred for 16 hours, and 20 ml ethyl acetate are added thereto. The product is washed four times with 20 ml water, the organic layer is separated, thereafter made anhydrous and evaporated to dryness. The residue is recrystallized from isopropyl alcohol:water and 0.15 g 1-(ethoxycarbonyloxy)ethyl ester of (R) 6β-[α-(1-methyl-2-formylhydrazino)phenylacetamido]penicillanic acid exactly like the acid of the previous Example is obtained.

EXAMPLE 15

1-(Ethoxycarbonyloxy)ethyl ester of (R) 6β-[α-(2-formylhydrazino)phenylacetamido]penicillanic acid To a solution of 13.28 g 1-(ethoxycarbonyloxy)ethyl ester of 6β-aminopenicillanic acid in 150 ml methylene chloride are added 40 ml propylene oxide; the product is cooled to −30° C., 8.85 g chloride hydrochloride of (R) α-hydrazinophenylacetic acid are added to the mixture, and it is kept under stirring for 1 hour at the same temperature. By evaporating to dryness and triturating the oily residue with diethyl ether, there are obtained 20 g 1-(ethoxycarbonyloxy)ethyl ester of (R) 6β-(α-hydrazinophenylacetamido)penicillanic acid hydrochloride melting at 108.4°–109.6° C.; $[\alpha]_D = +109.9°$ C. (c=1 in chloroform).

To a solution of 15 g 1-(ethoxycarbonyloxy)ethyl ester of (R) 6β-(α-hydrazinophenylacetamido)penicillanic acid in 150 ml pyridine cooled to 0° C., are slowly added 4.95 ml acetoformic anhydride in 30 ml chloroform. The mixture is stirred for 30 minutes at 0° C., for a further hour at ambient temperature, then 500 ml ethyl acetate are added thereto and it is washed four times with 100 ml water. The organic layer is made anhydrous and evaporated to dryness, the residue is taken up with petroleum ether until a gummy product is obtained, which is then purified by chromatography (silicagel, hexane:ethyl acetate, 1:1) to give 2.35 g 1-(ethoxycarbonyloxy)ethyl ester of (R) 6β-[α-(2-formylhydrazino)phenylacetamido]penicillanic acid melting at 58.6°–64.3° C.; $[\alpha]_D = +111.3°$ C. (c=1 in chloroform).

EXAMPLE 16

Pivaloyloxymethyl ester of (R) 6β-[α-(2-formylhydrazino)phenylacetamido]penicillanic acid Operating in a manner analogous to that previously described, starting from pivaloyloxymethyl ester of 6β-aminopenicillanic acid, pivaloyloxymethyl ester of (R) 6β-(α-hydrazinophenylacetamido)penicillanic acid is at first obtained and then pivaloyloxymethyl ester of (R) 6β-[α-(2-formylhydrazino)phenylacetamido]penicillanic acid is obtained, melting at 69.3°–74.8° C. (with decomposition).

EXAMPLE 17

(R) 6β-[α-(2-Formylhydrazino)phenylacetamido]penicillanic acid

To a solution of 6.57 g R(−)α-[1-(p.nitrobenzyloxycarbonyl)-2-formylhydrazino]phenylacetic acid (prepared as previously described) in 60 ml water, while stirring is added a solution of 0.95 g sodium carbonate, to the so obtained mixture are added 10 g of 5% palladium/calcium carbonate and hydrogen is bubbled in for 13 hours. The reaction mixture is filtered over celite, washed with chloroform, adjusted to pH 2 and concentrated until a precipitate is obtained, which is collected under vacuum in order to obtain 1.39 g R(−)α-(2-formylhydrazino)phenylacetic acid. The aqueous mother liquors, after evaporating to dryness, are extracted with tetrahydrofuran; the organic layer, after removal of the solvent, is triturated with diethyl ether. The solid is collected under vacuum and 0.85 g R(−) α-(2-formylhydrazino)phenylacetic acid is obtained, melting at 136.9° C.; $[\alpha]_D = 169°$ C. (c=1 in tetrahydrofuran).

To a solution of 3.4 g p.nitrobenzyl ester of 6β-aminopenicillanic acid in 20 ml tetrahydrofuran is added, while stirring at 4° C., a solution of 2 g dicyclohexylcarbodiimide, and 1.88 g R(−)α-(2-formylhydrazino)phenylacetic acid dissolved in 30 ml tetrahydrofuran are added dropwise to the mixture. Stirring is continued at 4° C. for 1 hour and then for a further 5 hours at ambient temperature. The insoluble is filtered off, the filtrate is evaporated to dryness, purified by chromatography (silicagel, hexane/ethyl acetate, 3:7) and 1.72 g p.nitrobenzyl ester of (R) 6β-[α-(2-formylhydrazino)phenylacetamido]penicillanic acid are obtained, melting at 84.9°–86.9° C.; $[\alpha]_D = +127°$ C. (c=1 in tetrahydrofuran).

To a solution of 0.5 g p.nitrobenzyl ester of (R) 6β-[α-(2-formylhydrazino)phenylacetamido]penicillanic acid in 8 ml tetrahydrofuran and 4 ml water are added 0.35 g 10% palladium over charcoal while stirring, and hydrogen is bubbled in for 7 hours. It is filtered over celite washing with tetrahydrofuran and 5% aqueous sodium bicarbonate. The clear aqueous liquors are washed five times with 10 ml ethyl acetate and adjusted to pH 2. The product is evaporated to dryness, the residue is taken up with tetrahydrofuran, filtered and evaporated to dryness. The oily residue is triturated with diethyl ether and collected in a vacuum to give 0.2 g (R) 6β-[α-(2-formylhydrazino)phenylacetamido]penicillanic acid melting at 145.5°–147.8° C. (with decomposition); $[\alpha]_D = +117.6°$ C. (c=1 in tetrahydrofuran).

EXAMPLES 18, 19

Operating in a manner similar to that described in Example 12, using (RS) α-hydrazinothienylacetic acid and (R) α-hydrazinophenylacetic acid, pivaloyloxymethyl ester of (R,S) 6β-[α-(1.2-diformylhydrazino)-2-thienylacetamido]penicillanic acid and pivaloyloxymethyl ester of (R) 6β-[α-(1.2-diformylhydrazino)phenylacetamido]penicillanic acid are obtained respectively, identical to that obtained in Examples 6 and 5.

We claim:
1. Formyl derivatives of hydrazinopenicillins of the formula

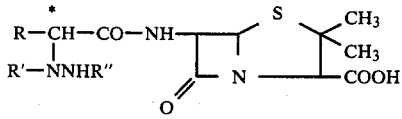

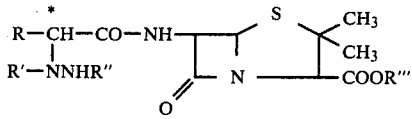

wherein R is thienyl or phenyl, R' is hydrogen, formyl or alkyl containing from 1 to 3 carbon atoms and R" is hydrogen or formyl, provided that at least one of R' and R" is a formyl group, the carbon atom with the asterisk indicating a center of asymmetry of the molecule, and pharmaceutically acceptable salts and esters thereof, as mixture or as separated epimers.

2. Formyl derivatives of hydrazinopenicillin according to claim 1 in which the pharmaceutically acceptable ester is the 1-(ethoxycarbonyloxy)ethyl ester.

3. Formyl derivatives of hydrazinopenicillin according to claim 1 in which the pharmaceutically acceptable ester is the pivaloyloxymethyl ester.

4. (R) 6β-[α-(2-Formyl-1-methylhydrazino)-phenylacetamido]penicillanic acid.

5. (R) 6β-[α-(1.2-Diformylhydrazino)-phenylacetamido]penicillanic acid.

6. (R) 6β-[α-(2-Formylhydrazino)phenylacetamido]penicillanic acid.

7. 1-(Ethoxycarbonyloxy)ethyl ester of (R) 6β-[α-(2-formylhydrazino)phenylacetamido]penicillanic acid.

8. Process for the preparation of formyl derivatives of hydrazinopenicillin of the formula wherein R is thienyl or phenyl, R' is hydrogen, alkyl containing from 1 to 3 carbon atoms or formyl, R" is hydrogen or formyl, provided that at least one of R' and R" is a formyl group, R''' is hydrogen or a pharmaceutically acceptable substituent, the carbon atom with the asterisk indicating a center of asymmetry of the molecule, in the form of a mixture or separated epimers, wherein the corresponding hydrazinopenicillin of the formula

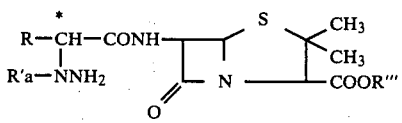

wherein R and R''' are as defined above, and R'a is hydrogen or alkyl having from 1 to 3 carbon atoms, the carbon atom with the asterisk indicating a center of asymmetry of the molecule, in the form of a mixture or separated epimers, is reacted under anhydrous conditions with acetoformic anhydride to give the desired compounds.

* * * * *

UNITED STATES PATENT AND TRADEMARK OFFICE
CERTIFICATE OF CORRECTION

PATENT NO.   : 4,329,285
DATED        : May 11, 1982
INVENTOR(S)  : Goffredo BOLIS et al It is certified that error appears in the above—identified patent and that said Letters Patent is hereby corrected as shown below:

Column 2, line 13, after "a pharmaceutically acceptable" insert -- substituent --.

Column 2, line 27, after "formylated," change "at" to -- of --.

Column 5, line 55, change "6β-amminopenicillanic" to -- 6β-aminopenicillanic --.

Signed and Sealed this

Fourteenth Day of September 1982

[SEAL]

Attest:

GERALD J. MOSSINGHOFF

Attesting Officer   Commissioner of Patents and Trademarks